United States Patent
Ishii et al.

(10) Patent No.: US 11,718,831 B2
(45) Date of Patent: Aug. 8, 2023

(54) REAGENT FOR DIFFERENTIATING SOMATIC CELLS INTO ALVEOLAR EPITHELIAL CELLS, AND USE OF SAID REAGENT

(71) Applicant: KEIO UNIVERSITY, Tokyo (JP)

(72) Inventors: Makoto Ishii, Tokyo (JP); Tomoko Betsuyaku, Tokyo (JP); Minoru Ko, Tokyo (JP); Masaki Ieda, Tokyo (JP); Masaya Yotsukura, Tokyo (JP); Hisao Asamura, Tokyo (JP); Ahmed Hegab, Tokyo (JP); Yuhki Nakatake, Tokyo (JP); Mayumi Oda, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 708 days.

(21) Appl. No.: 16/606,294

(22) PCT Filed: Apr. 19, 2018

(86) PCT No.: PCT/JP2018/016126
§ 371 (c)(1),
(2) Date: Jan. 28, 2020

(87) PCT Pub. No.: WO2018/194124
PCT Pub. Date: Oct. 25, 2018

(65) Prior Publication Data
US 2020/0318074 A1    Oct. 8, 2020

(30) Foreign Application Priority Data
Apr. 20, 2017 (JP) ................................. 2017-083814

(51) Int. Cl.
| | |
|---|---|
| *C12N 5/02* | (2006.01) |
| *C12N 15/79* | (2006.01) |
| *C12N 15/63* | (2006.01) |
| *C07H 21/04* | (2006.01) |
| *C12N 5/071* | (2010.01) |
| *A61P 11/00* | (2006.01) |
| *A61P 31/16* | (2006.01) |
| *A61K 35/42* | (2015.01) |
| *C12N 15/86* | (2006.01) |

(52) U.S. Cl.
CPC ............ *C12N 5/0688* (2013.01); *A61K 35/42* (2013.01); *A61P 11/00* (2018.01); *A61P 31/16* (2018.01); *C12N 15/86* (2013.01); *C12N 2501/10* (2013.01); *C12N 2501/999* (2013.01); *C12N 2510/00* (2013.01); *C12N 2513/00* (2013.01); *C12N 2740/10043* (2013.01)

(58) Field of Classification Search
CPC ........ C12N 15/79; C12N 15/85; C12N 15/86; C12N 15/63; C12N 2510/00; C12N 2506/00; C12N 2506/1307; C07H 21/04
See application file for complete search history.

(56) References Cited

U.S. PATENT DOCUMENTS

2018/0051256 A1   2/2018  Gotoh et al.

FOREIGN PATENT DOCUMENTS

| | | | |
|---|---|---|---|
| WO | 2010119819 A1 | 10/2012 | |
| WO | 2015/178496 A1 | 11/2015 | |
| WO | WO 2015/173578 A1 | * 11/2015 | |
| WO | 2016/143803 A1 | 9/2016 | |
| WO | 2016143803 A1 | 9/2019 | |

OTHER PUBLICATIONS

Li et al., 2014, Journal of Hematology & Oncology, 7:50, p. 1-18.*
Sommer et al., 2013, J. Cell. Physiol., vol. 228, p. 267-275.*
Zhang et al., 2012, Cell Cycle, vol. 11, No. 24, p. 1-9.*
Su et al., 2020, Journal of Animal Science, vol. 98, No. 11, p. 1-15.*
International Search Report in PCT Application No. PCT/JP2018/016126 (English Translation), dated Jul. 17, 2018.
Roszell, B., et al., "Efficient Derivation of Alveolar Type II Cells from Embryonic Stem Cells for in Vivo Application", Tissue Eng. Part A. 15 (11), 3351-3365, 2009.
Gotoh S. et al., "Generation of Alveolar Epithelial Spheroids via Isolated Progenitor Cells from Human Pluripotent Stem Cells", Stem Cell Reports, 3 (3), 394-403, 2014.
Japanese Office Action in related JP Application No. 2019-513683, dated Sep. 9, 2022 (English Translation Provided).

* cited by examiner

*Primary Examiner* — Shin Lin Chen
(74) *Attorney, Agent, or Firm* — Thomas | Horstemeyer, LLP (57) ABSTRACT

A reagent for differentiating somatic cells into alveolar epithelial cells includes an NK2 homeobox family gene expression vector, and a Fox family gene expression vector, a method for manufacturing alveolar epithelial cells, the method including forcing a somatic cell to express an NK2 homeobox family gene and a Fox family gene and culturing the somatic cell after forced expression, an alveolar epithelial cell manufactured by the manufacturing method, and a cell medicine including the alveolar epithelial cell.

8 Claims, 11 Drawing Sheets

REAGENT FOR DIFFERENTIATING SOMATIC CELLS INTO ALVEOLAR EPITHELIAL CELLS, AND USE OF SAID REAGENT

TECHNICAL FIELD

The present invention relates to a reagent for differentiating somatic cells into alveolar epithelial cells, and use of the reagent. More specifically, the present invention relates to a reagent for differentiating somatic cells into alveolar epithelial cells, a method for manufacturing alveolar epithelial cells, an alveolar epithelial cell, and a cell medicine.

Priority is claimed on Japanese Patent Application No. 2017-083814, filed Apr. 20, 2017, the content of which is incorporated herein by reference.

BACKGROUND ART

For example, idiopathic pulmonary fibrosis is an intractable disease for which no effective treatment method is known. In the lungs of patients with idiopathic pulmonary fibrosis, the alveoli become fibrotic, the stroma through which oxygen and carbon dioxide pass becomes thicker and harder, and thereby gas exchange cannot be performed well. As a method for treating idiopathic pulmonary fibrosis, regeneration or transplantation of alveolar epithelial cells is expected.

In the related art, examinations on use of stem cells such as embryonic stem cells (ES cells) and induced pluripotent stem cells (iPS cells) for regenerative medicine of lung cells have been performed. For example, Non-Patent Document 1 discloses a method for differentiating ES cells into alveolar epithelial cells. In addition, Non-Patent Document 2 discloses a method for differentiating iPS cells into alveolar epithelial cells.

CITATION LIST

Non Patent Literature

[Non-Patent Document 1]
Roszell B. et al., Efficient derivation of alveolar type II cells from embryonic stem cells for in vivo application, Tissue Eng. Part A. 15 (11), 3351-3365, 2009.
[Non-Patent Document 2]
Gotoh S. et al., Generation of Alveolar Epithelial Spheroids via Isolated Progenitor Cells from Human Pluripotent Stem Cells, Stem Cell Reports, 3 (3), 394-403, 2014.

SUMMARY OF INVENTION

Technical Problem

However, in the method for obtaining alveolar epithelial cells from stem cells, the stem cells need to differentiate through a process of several stages to follow the development process. For this reason, time and labor are needed to prepare alveolar epithelial cells, and it may be difficult to clinically apply this method. In addition, because stem cells having an infinite proliferative ability are used, tumors such as teratoid tumors may be formed after the alveolar epithelial cells are transplanted into patients. An object of the present invention is to provide a technique for manufacturing alveolar epithelial cells more simply without using stem cells.

Solution to Problem

The present invention includes the following aspects.

[1] A reagent for differentiating somatic cells into alveolar epithelial cells, the reagent including an NK2 homeobox family gene expression vector, and a Fox family gene expression vector.

[2] The reagent for differentiating somatic cells into alveolar epithelial cells according to [1], the reagent including the NK2 homeobox family gene expression vector, the Fox family gene expression vector, and a Gata family gene expression vector.

[3] The reagent for differentiating somatic cells into alveolar epithelial cells according to [2], in which the Gata family gene is a Gata Binding Protein 6 (Gata6) gene.

[4] The reagent for differentiating somatic cells into alveolar epithelial cells according to any one of [1] to [3], in which the NK2 homeobox family gene is an NK2 Homeobox 1 (Nkx2-1) gene.

[5] The reagent for differentiating somatic cells into alveolar epithelial cells according to any one of [1] to [4], in which the Fox family gene is a Forkhead Box A1 (Foxa1) gene or a Forkhead Box A2 (Foxa2) gene.

[6] A method for manufacturing alveolar epithelial cells, the method including a step of forcing a somatic cell to express an NK2 homeobox family gene and a Fox family gene; and a step of culturing the somatic cell after forced expression.

[7] The manufacturing method according to [6], in which a Gata family gene is further forcibly expressed in the forcing the somatic cell to express the NK2 homeobox family gene and the Fox family gene.

[8] The manufacturing method according to [6] or [7], in which the culturing step is performed by three-dimensional culture.

[9] The manufacturing method according to any one of [6] to [8], in which the culturing step is performed in the presence of dexamethasone and a Fibroblast Growth Factor (FGF) family protein.

[10] An alveolar epithelial cell manufactured by the manufacturing method according to any one of [6] to [9].

[11] A cell medicine including the alveolar epithelial cell according to [10] as an active ingredient.

Advantageous Effects of Invention

According to the present invention, it is possible to provide a technique for manufacturing alveolar epithelial cells more simply without using stem cells.

BRIEF DESCRIPTION OF DRAWINGS (a) of FIG. 1 is a graph showing results of measuring an mRNA expression level of a Surfactant Protein C (Sftpc) gene in a fibroblast into which a gene was introduced in Experimental Example 1. (b) of FIG. 1 is a graph showing results of measuring an mRNA expression level of a Secretoglobin Family 1A Member 1 (Scgb1a1) gene in a fibroblast into which a gene was introduced in Experimental Example 1.

(a) of FIG. 3 is a graph showing results of measuring an mRNA expression level of an Sftpc gene in a fibroblast into which a gene was introduced in Experimental Example 3.

(b) of FIG. 3 is a graph showing results of measuring an mRNA expression level of an Scgb1a1 gene in a fibroblast into which a gene was introduced in Experimental Example 3.

(a) of FIG. 4 is a graph showing results of measuring an mRNA expression level of an Sftpc gene in a fibroblast into which a gene was introduced in Experimental Example 4. (b) of FIG. 4 is a graph showing results of measuring an mRNA expression level of an Scgb1a1 gene in a fibroblast into which a gene was introduced in Experimental Example 4.

(a) to (c) of FIG. 5 are photomicrographs of cells 26 days after gene introduction in Experimental Example 6. (a) is a bright-field observation image, (b) is a fluorescence micrograph of observed GFP fluorescence, and (c) is an image obtained by merging the images of (a) and (b).

(a) of FIG. 6 is a representative electron micrograph of a GFP-fluorescence-positive cell observed in Experimental Example 6. (b) of FIG. 6 is an enlarged photograph of an area enclosed by a square in (a).

(a) of FIG. 7 is an image obtained by introducing a combination of a total of three genes, which are an Nkx2-1 gene, a Foxa1 gene, and a Gata6 gene, into a fibroblast; performing microscopic observation 12 days after the gene introduction; and merging a bright-field observation image and a fluorescence micrograph of GFP fluorescence observed in Experimental Example 7. (b) of FIG. 7 is a fluorescence micrograph showing a result of staining an SFTPC protein by fluorescent immunostaining in Experimental Example 7. (c) of FIG. 7 is a fluorescence micrograph showing a result of staining an Aquaporin 5 (Aqp5) protein by fluorescent immunostaining in Experimental Example 7.

(a) of FIG. 8 is a graph showing transitional changes in body weight of mice in Experimental Example 8. (b) of FIG. 8 is a graph showing transitional changes in a survival rate of mice in Experimental Example 8.

(a) and (b) of FIG. 9 are optical micrographs of a hematoxylin-eosin-stained tissue section of a mouse lung in Experimental Example 8.

(a) and (b) of FIG. 10 are fluorescence micrographs showing results of a fluorescent immunostaining of tissue section of a mouse lung in Experimental Example 8.

DESCRIPTION OF EMBODIMENTS

[Reagent for Differentiating Somatic Cells into Alveolar Epithelial Cells]

In one embodiment, the present invention provides a reagent for differentiating somatic cells into alveolar epithelial cells, and the reagent including an NK2 homeobox family gene expression vector, and a Fox family gene expression vector. The differentiation reagent of the present embodiment can also be said to be a composition including the NK2 homeobox family gene expression vector and the Fox family gene expression vector. Alternatively, the differentiation reagent can be said to be a kit including the NK2 homeobox family gene expression vector and the Fox family gene expression vector.

As will be described later in Examples, the inventors of the present invention have shown that it is possible to directly induce differentiation of a fibroblast into an alveolar epithelial cell without using stem cells by forcing the fibroblast to express an NK2 homeobox family gene and a Fox family gene. Accordingly, according to the differentiation reagent of the present embodiment, it is possible to manufacture alveolar epithelial cells more simply without using stem cells.

In the differentiation reagent of the present embodiment, examples of somatic cells include fibroblasts, cells derived from blood cells, and the like.

The differentiation reagent of the present embodiment may be in any form as long as the NK2 homeobox family gene and the Fox family gene can be expressed in somatic cells. For example, one expression vector may include the NK2 homeobox family gene and the Fox family gene in a manner capable of expressing the genes. In this case, the vector can be said to be the NK2 homeobox family gene expression vector or the Fox family gene expression vector. Alternatively, the NK2 homeobox family gene expression vector and the Fox family gene expression vector may each be included as separate vectors.

In the differentiation reagent of the present embodiment, a gene of a somatic cell line may be used as the NK2 homeobox family gene and the Fox family gene. For example, a human gene may be used in a case where a somatic cell is a human cell, or a mouse gene may be used in a case where a somatic cell is a mouse cell.

Examples of NK2 homeobox family genes include an Nkx2-1 gene, an Nkx2-2 gene, an Nkx2-5 gene, an Nkx6-1 gene, and the like. Among them, the Nkx2-1 gene is preferable. An NCBI Gene ID (https://www.ncbi.nlm.nih.gov/gene/) of a mouse Nkx2-1 gene is 21869, and an MGI ID (http://www.informatics.jax.org/) thereof is 108067. In addition, an NCBI Gene ID (https://www.ncbi.nlm.nih.gov/gene/) of a human NKX2-1 gene is 7080. One kind of NK2 homeobox family gene may be used alone, or two or more kinds thereof may be used in combination.

Examples of Fox family genes include a Foxa1 gene, a Foxa2 gene, a Foxa3 gene, a Foxb1 gene, a Foxb2 gene, a Foxc1 gene, a Foxc2 gene, a Foxd1 gene, a Foxd2 gene, a Foxd3 gene, a Foxd4 gene, a Foxd5 gene, a Foxd6 gene, a Foxd7 gene, a Foxd8 gene, a Foxe1 gene, a Foxe2 gene, a Foxe3 gene, a Foxf1 gene, a Foxf2 gene, a Foxg1 gene, a Foxh1 gene, a Foxi1 gene, a Foxj1 gene, a Foxj2 gene, a Foxj3 gene, a Foxk1 gene, a Foxm1 gene, a Foxn1 gene, a Foxn2 gene, a Foxn3 gene, a Foxn4 gene, a Foxn5 gene, a Foxn6 gene, a Foxo1 gene, a Foxo3a gene, a Foxo4 gene, a Foxp1 gene, a Foxp2 gene, a Foxp3 gene, a Foxq1 gene, and the like. Among them, the Foxa1 gene and the Foxa2 gene are preferable. An NCBI Gene ID of a mouse Foxa1 gene is 15375, and an MGI ID thereof is 1347472. In addition, an NCBI Gene ID of a human FOXA1 gene is 3169. Furthermore, an NCBI Gene ID of a mouse Foxa2 gene is 15376, and an MGI ID thereof is 1347476. Furthermore, an NCBI Gene ID of a human FOXA2 gene is 3170. One kind of Fox family gene may be used alone, or two or more kinds thereof may be used in combination.

The differentiation reagent of the present embodiment may further include a Gata family gene expression vector. That is, the differentiation reagent of the present embodiment may include the NK2 homeobox family gene expression vector, the Fox family gene expression vector, and the Gata family gene expression vector.

As will be described later in Examples, in a case where the differentiation reagent includes the Gata family gene expression vector, efficiency of differentiation-inducing fibroblasts into alveolar epithelial cells tends to further increase.

In the differentiation reagent of the present embodiment, one expression vector may include the NK2 homeobox family gene, the Fox family gene, and a Gata family gene in a manner capable of expressing the genes. In this case, the vector can be said to be the NK2 homeobox family gene expression vector, the Fox family gene expression vector, or the Gata family gene expression vector.

Alternatively, the differentiation reagent of the present embodiment may include one expression vector having any two kinds among three kinds of the NK2 homeobox family gene, the Fox family gene, and the Gata family gene in a manner capable of expressing the genes, and include an expression vector having the residual one kind of the genes.

Alternatively, the differentiation reagent of the present embodiment may include the NK2 homeobox family gene expression vector, the Fox family gene expression vector, and the Gata family gene expression vector, as separate vectors.

In the differentiation reagent of the present embodiment, a gene of a somatic cell line may be used as the Gata family gene. For example, a human gene may be used in a case where a somatic cell is a human cell, or a mouse gene may be used in a case where a somatic cell is a mouse cell.

Examples of Gata family genes include a Gata6 gene, a Gata1 gene, a Gata4 gene, and the like. Among them, the Gata6 gene is preferable. An NCBI Gene ID of a mouse Gata6 gene is 14465, and an MGI ID thereof is 107516. In addition, an NCBI Gene ID of a human GATA6 gene is 2627. One kind of Gata family gene may be used alone, or two or more kinds thereof may be used in combination.

In the differentiation reagent of the present embodiment, the expression vector may be a viral vector. Viral vectors have high gene introduction efficiency and are easy to use. Examples of viral vectors include a retroviral vector, a lentiviral vector, an adeno-associated viral vector, an adenoviral vectors, and the like.

[Method for Manufacturing Alveolar Epithelial Cells]

In one embodiment, the present invention provides a method for manufacturing alveolar epithelial cells, the method including a step of forcing a somatic cell to express an NK2 homeobox family gene and a Fox family gene; and a step of culturing the somatic cell after forced expression.

As will be described later in Examples, the inventors of the present invention have shown that it is possible to directly induce differentiation of a fibroblast into an alveolar epithelial cell without using stem cells by forcing the fibroblast to express an NK2 homeobox family gene and a Fox family gene. Accordingly, according to the manufacturing method of the present embodiment, it is possible to manufacture alveolar epithelial cells more simply without using stein cells.

In the method of the present embodiment, somatic cells are the same as those described above. In addition, the method for forcibly expressing the NK2 homeobox family gene and the Fox family gene is not particularly limited. For example, the method may be a method of introducing the NK2 homeobox family gene expression vector and the Fox family gene expression vector into a somatic cell. Alternatively, the method may be a method of adding a compound or the like which induces expression of the NK2 homeobox family gene, and a compound or the like which induces expression of the Fox family gene into a medium of somatic cells.

The NK2 homeobox family gene, the Fox family gene, and an expression vector are the same as those described above.

In addition, in the step of forcibly expressing the NK2 homeobox family gene and the Fox family gene, a Gata family gene may further be forcibly expressed. As will be described later in Examples, in a case where the Gata family gene is forcibly expressed in addition to the NK2 homeobox family gene and the Fox family gene in somatic cells, efficiency of differentiation-inducing somatic cells into alveolar epithelial cells tends to further increase.

A method for forcibly expressing the Gata family gene is not particularly limited, and it may be, for example, a method of introducing the Gata family gene expression vector into a somatic cell, or may be, for example, a method of adding a compound or the like which induces expression of the Gata family gene into a medium of somatic cells. The Gata family gene and an expression vector are the same as those described above.

In the manufacturing method of the present embodiment, the step of culturing somatic cells after forcing the somatic cells to express the NK2 homeobox family gene and the Fox family gene, and if necessary, the Gata family gene, is preferably performed by three-dimensional culture. A method for three-dimensional culture is not particularly limited, and examples thereof include a method using a Matrigel, a method using a collagen, a method using a laminin, and the like.

As will be described later in Examples, efficiency of differentiation-inducing somatic cells into alveolar epithelial cells tends to further increase when the step of culturing somatic cells that have undergone gene introduction by three-dimensional culture is performed.

In addition, the step of culturing somatic cells that have undergone gene introduction is preferably performed in the presence of dexamethasone and an FGF family protein. As will be described later in Examples, efficiency of differentiation-inducing somatic cells into alveolar epithelial cells tends to further increase when the step of culturing somatic cells that have undergone gene introduction is performed in the presence of the dexamethasone and the FGF family protein.

Examples of FGF family proteins include FGF7, FGF2, FGF10, and the like. Among them, FGF7 is preferable. An NCBI Reference Sequence of a mouse FGF7 protein is NP_032034, and an NCBI Reference Sequence of a human FGF7 protein is NP_002000. In addition, an NCBI Reference Sequence of a mouse FGF2 protein is NP_032032.1, and an NCBI Reference Sequence of a human FGF2 protein is NP_001997. Furthermore, an NCBI Reference Sequence of a mouse FGF10 protein is NP_032028.1, and an NCBI Reference Sequence of a human FGF10 protein is NP_004456.1.

In the step of culturing somatic cells that have undergone gene introduction, a protein kinase A activator such as 8-Br-cAMP; an inhibitor of cAMP phosphodiesterase or cGMP phosphodiesterase, such as IBMX; an inhibitor of Glycogen synthase kinase 3 (GSK3), such as CHIR-99021; or the like may be contained as a medium in addition to the dexamethasone and the FGF family protein.

[Alveolar Epithelial Cell]

In one embodiment, the present invention provides an alveolar epithelial cell manufactured by the manufacturing method described above. The alveolar epithelial cell of the present embodiment can be used for treating diseases for which transplantation of alveolar epithelial cells is effective, such as idiopathic interstitial pneumonia, pneumonia caused by influenza and bacteria, acute respiratory distress syndrome (ARDS), and chronic obstructive pulmonary disease (COPD).

In addition, the alveolar epithelial cell of the present embodiment is not a cell differentiated by normal development but is a cell manufactured by forcing somatic cells to express a specific gene. For this reason, gene expression profiles or the like thereof are predicted to be different from those of a normal alveolar epithelial cell. However, it is difficult to specify differences in gene expression profiles that can distinguish the alveolar epithelial cell of the present embodiment from a normal alveolar epithelial cell.

[Cell Medicine]

In one embodiment, the present invention provides a cell medicine including the alveolar epithelial cells manufactured by the manufacturing method described above as an active ingredient. The cell medicine of the present embodiment can be used for treating diseases for which transplantation of alveolar epithelial cells is effective, such as idiopathic interstitial pneumonia, pneumonia caused by influenza and bacteria, acute respiratory distress syndrome (ARDS), and chronic obstructive pulmonary disease (COPD). In the cell medicine of the present embodiment, the alveolar epithelial cell may be a cell manufactured from somatic cells of a patient himself or herself, or may be a cell manufactured from somatic cells of a third party having a major histocompatibility complex compatible with that of a patient.

OTHER EMBODIMENTS

In one embodiment, the present invention provides a method for treating a pulmonary disease, the method including transplanting an effective amount of alveolar epithelial cells manufactured by the manufacturing method described above to patients in need of treatment. Examples of pulmonary diseases include idiopathic interstitial pneumonia, pneumonia caused by influenza and bacteria, acute respiratory distress syndrome (ARDS), chronic obstructive pulmonary disease (COPD), and the like.

In one embodiment, the present invention provides use of alveolar epithelial cells manufactured by the manufacturing method described above for treating pulmonary diseases. Examples of pulmonary diseases include idiopathic interstitial pneumonia, pneumonia caused by influenza and bacteria, acute respiratory distress syndrome (ARDS), chronic obstructive pulmonary disease (COPD), and the like.

In one embodiment, the present invention provides use of alveolar epithelial cells manufactured by the manufacturing method described above for manufacturing a therapeutic agent for pulmonary diseases. Examples of pulmonary diseases include idiopathic interstitial pneumonia, pneumonia caused by influenza and bacteria, acute respiratory distress syndrome (ARDS), chronic obstructive pulmonary disease (COPD), and the like.

EXAMPLES

Next, the present invention will be described in more detail by showing experimental examples, but the present invention is not limited to the following experimental examples.

Experimental Example 1

(Examination 1 of Factors Necessary for Differentiation from Somatic Cells to Alveolar Epithelial Cells)

Factors necessary for differentiation from somatic cells to alveolar epithelial cells were examined. Fibroblasts derived from a mouse fetus were used as somatic cells. First, using a retrovirus expression vector, 14 types of mouse genes shown in Table 1 were simultaneously introduced into mouse fibroblasts and overexpressed. Table 1 also shows NCBI Gene IDs and MGI IDs of respective genes.

TABLE 1

| No. | Gene | NCBI Gene ID | MGI ID |
|---|---|---|---|
| 1 | NK2 Homeobox 1 (Nkx2-1) | 21869 | 108067 |
| 2 | Forkhead Box A1 (Foxa1) | 15375 | 1347472 |
| 3 | Forkhead Box A2 (Foxa2) | 15376 | 1347476 |
| 4 | Forkhead Box J1 (Foxj1) | 15223 | 1347474 |
| 5 | Transcription Factor 21 (Tcf21) | 21412 | 1202715 |
| 6 | Homeobox A5 (Hoxa5) | 15402 | 96177 |
| 7 | SRY-Box 17 (Sox17) | 20671 | 107543 |
| 8 | Gata Binding Protein 6 (Gata6) | 14465 | 107516 |
| 9 | T-Box 4 (Tbx4) | 21387 | 102556 |
| 10 | Gata Binding Protein 5 (Gata5) | 14464 | 109497 |
| 11 | Forkhead Box F1 (Foxf1) | 15227 | 1347470 |
| 12 | Forkhead Box L1 (Foxl1) | 14241 | 1347469 |
| 13 | GL1 Family Zinc Finger 2 (Gli2) | 14633 | 95728 |
| 14 | GL1 Family Zinc Finger 3 (Gli3) | 14634 | 95729 |

Subsequently, 7 days after the gene introduction, expression levels of a Surfactant Protein C (Sftpc) gene and a Secretoglobin Family 1A Member 1 (Scgb1a1) gene, which are markers for alveolar epithelial cells, were measured by quantitative RT-PCR. In addition, as a control, fibroblasts into which a retrovirus expression vector of a green fluorescent protein (GFP) was introduced instead of the genes shown in Table 1 were used. Furthermore, an NCBI Gene ID of a mouse Sftpc gene is 20389, and an MGI ID thereof is 109517. Furthermore, an NCBI Gene ID of a mouse Scgb1a1 gene is 22287, and an MGI ID thereof is 98919.

Figure 1:
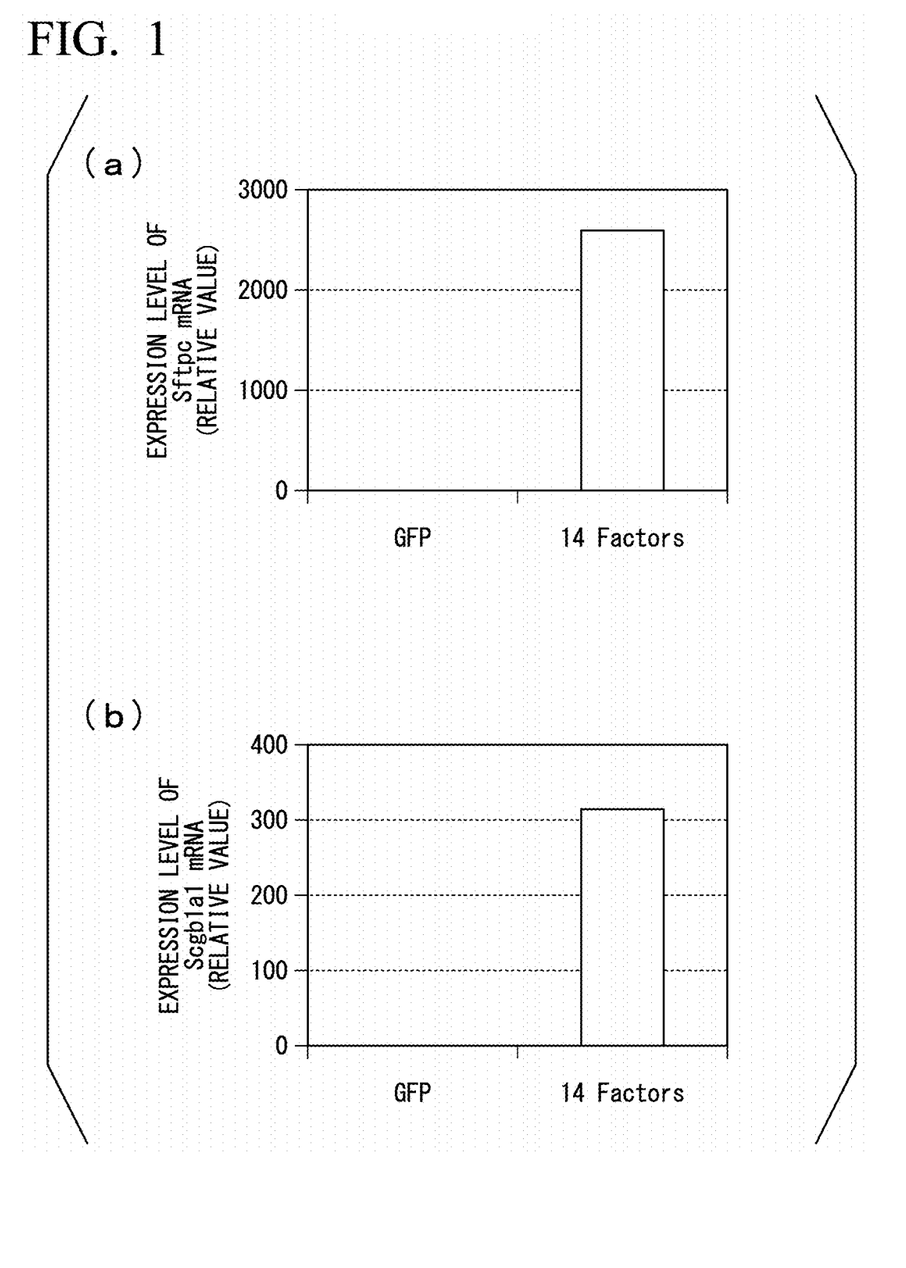

(a) of FIG. 1 is a graph showing results of measuring an mRNA expression level of an Sftpc gene. In addition, (b) of FIG. 1 is a graph showing results of measuring an mRNA expression level of an Scgb1a1 gene. In (a) and (b) of FIG. 1, the letter "GFP" indicates a result of the control cell, and the letter "14 Factors" indicates a result of introducing the 14 types of genes shown in Table 1.

As a result, it became clear that, in the fibroblasts into which the 14 types of genes shown in Table 1 were introduced, an mRNA expression level of the Sftpc gene increased 2000 times or more, and an mRNA expression level of the Scgb1a1 gene increased 300 times or more those of the control.

Experimental Example 2

(Examination 2 of Factors Necessary for Differentiation from Somatic Cells to Alveolar Epithelial Cells)

Factors necessary for differentiation from somatic cells to alveolar epithelial cells were examined in more details. Specifically, first, an expression level of the Sftpc gene, which is a marker of alveolar epithelial cells, was measured by quantitative RT-PCR in the same manner as in Experimental Example 1 except that 13 types of genes obtained by removing one gene from each of the 14 types of genes shown in Table 1 were introduced into mouse fibroblasts. In addition, as a control, fibroblasts into which a retrovirus expression vector of a GFP was introduced instead of the genes shown in Table 1 were used.

Figure 2:
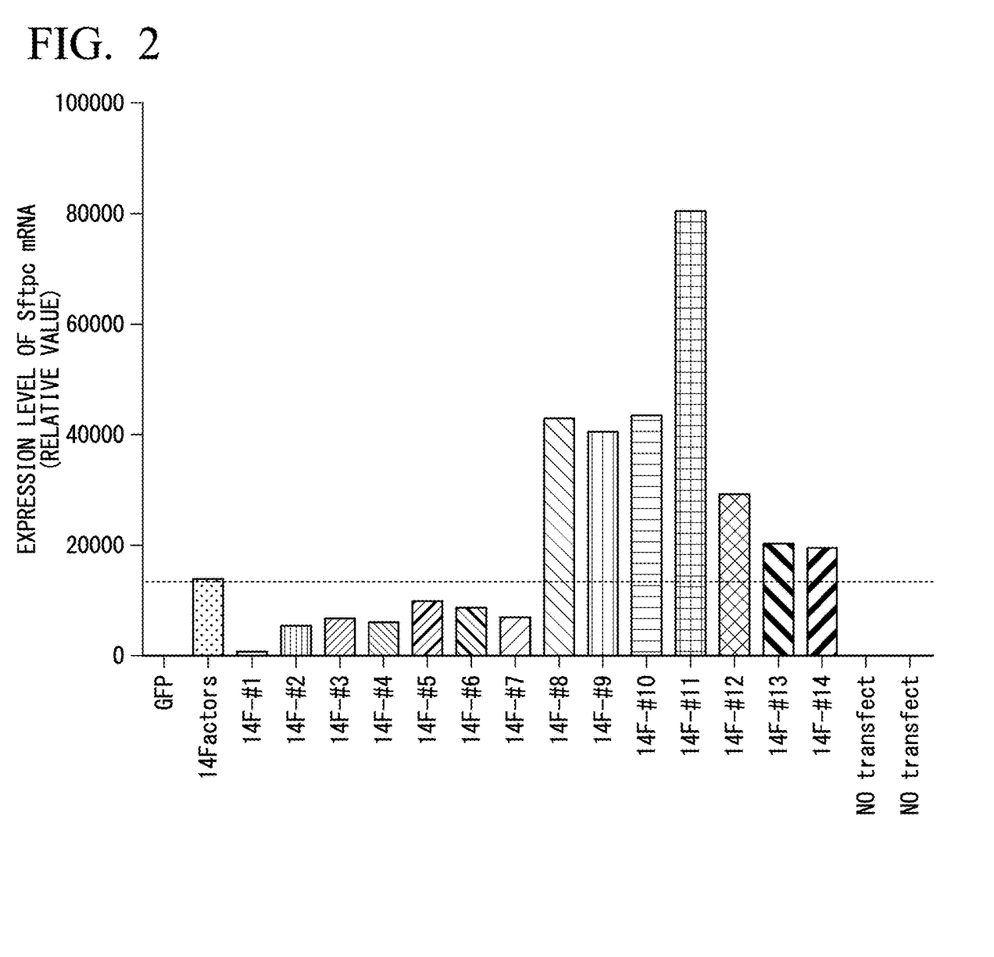
FIG. 2 is a graph showing results of measuring an mRNA expression level of an Sftpc gene in a fibroblast into which a combination of respective genes was introduced in Experimental Example 2.

FIG. 2 is a graph showing results of measuring an mRNA expression level of an Sftpc gene in a fibroblast into which a combination of respective genes was introduced. In FIG. 2, the letter "GFP" indicates a result of the control cell, and the letter "14 Factors" indicates a results of introducing all of the 14 types of genes shown in Table 1. In addition, the letter "14F-#1" indicates a result of introducing 13 types of genes obtained by excluding the gene of No. 1 in Table 1 from the 14 types of genes shown in Table 1, and the same applies to the residual letters. Furthermore, the letter "NO transfect" indicates a result of fibroblasts into which no gene was introduced.

As a result, it became clear that an mRNA expression level of the Sftpc gene decreases in a case of removing the expression vector of the factor of No. 1 (an Nkx2-1 gene) shown in Table 1. This result indicates that expression of the Nkx2-1 gene is essential for differentiation-induction from fibroblasts to alveolar epithelial cells.

Experimental Example 3

(Examination 3 of Factors Necessary for Differentiation from Somatic Cells to Alveolar Epithelial Cells)

Based on the results of Experimental Example 2, it became clear that expression of the Nkx2-1 gene is essential for differentiation from somatic cells to alveolar epithelial cells. Herein, a combination of an Nkx2-1 gene, and one gene selected from 13 types of genes shown in Table 1 excluding the Nkx2-1 gene was introduced into mouse fibroblasts, and expression levels of the Sftpc gene and the Scgb1a1 gene, which are markers of alveolar epithelial cells, were measured by quantitative RT-PCR. In addition, as a control, fibroblasts into which a retrovirus expression vector of a GFP was introduced instead of the genes shown in Table 1 were used.

Figure 3:
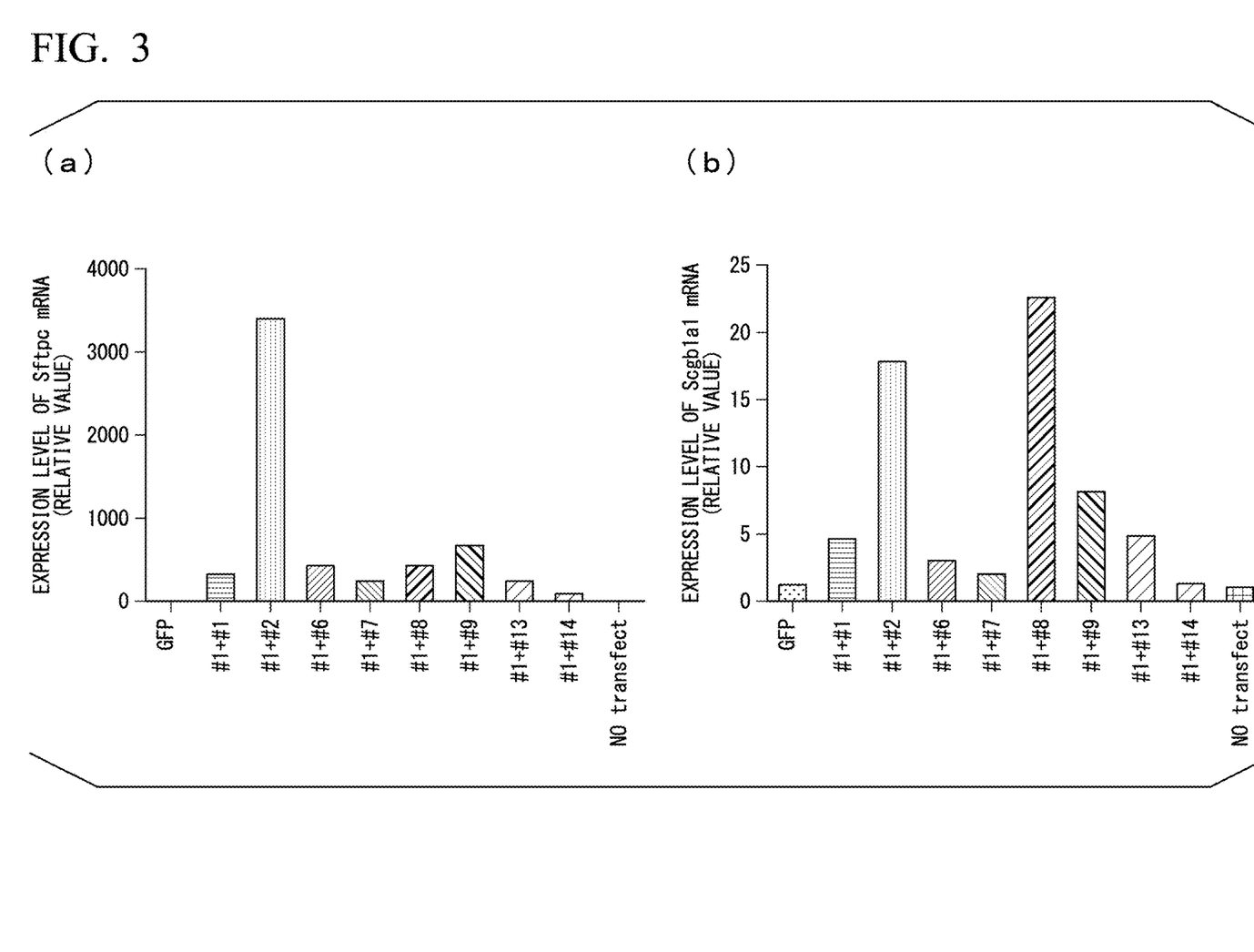

(a) of FIG. 3 is a graph showing results of measuring an mRNA expression level of an Sftpc gene. In addition, (b) of FIG. 3 is a graph showing results of measuring an mRNA expression level of an Scgb1a1 gene. In (a) and (b) of FIG. 3, the letter "GFP" indicates a result of the control cell, the letter "#1+#2" indicates a result of introducing a combination of the gene of No. 1 and the gene of No. 2 in Table 1, and the same applies to the residual letters. Furthermore, the letter "NO transfect" indicates a result of fibroblasts into which no gene was introduced.

As a result, it became clear that, in the fibroblasts into which the factor of No. 2 (a Foxa1 gene), the factor of No. 8 (a Gata6 gene), and the like were introduced in combination with the Nkx2-1 gene, expression levels of the Sftpc gene and the Scgb1a1 gene increased. This result indicates that expression of the combination of these genes is important for differentiation-induction from fibroblasts into alveolar epithelial cells.

Experimental Example 4

(Examination 4 of Factors Necessary for Differentiation from Somatic Cells to Alveolar Epithelial Cells)

Based on the results of Experimental Examples 2 and 3, factors necessary for differentiation from somatic cells to alveolar epithelial cells were further examined. Specifically, various combinations of the factor of No. 1 (an Nkx2-1 gene), the factor of No. 2 (a Foxa1 gene), the factor of No. 3 (a Foxa3 gene), and the factor of No. 8 (a Gata6 gene) shown in Table 1 were introduced into mouse fibroblasts, and expression levels of the Sftpc gene and the Scgb1a1 gene, which are markers of alveolar epithelial cells, were measured by quantitative RT-PCR. In addition, as a control, fibroblasts into which a retrovirus expression vector of a GFP was introduced instead of the genes shown in Table 1 were used.

Figure 4:
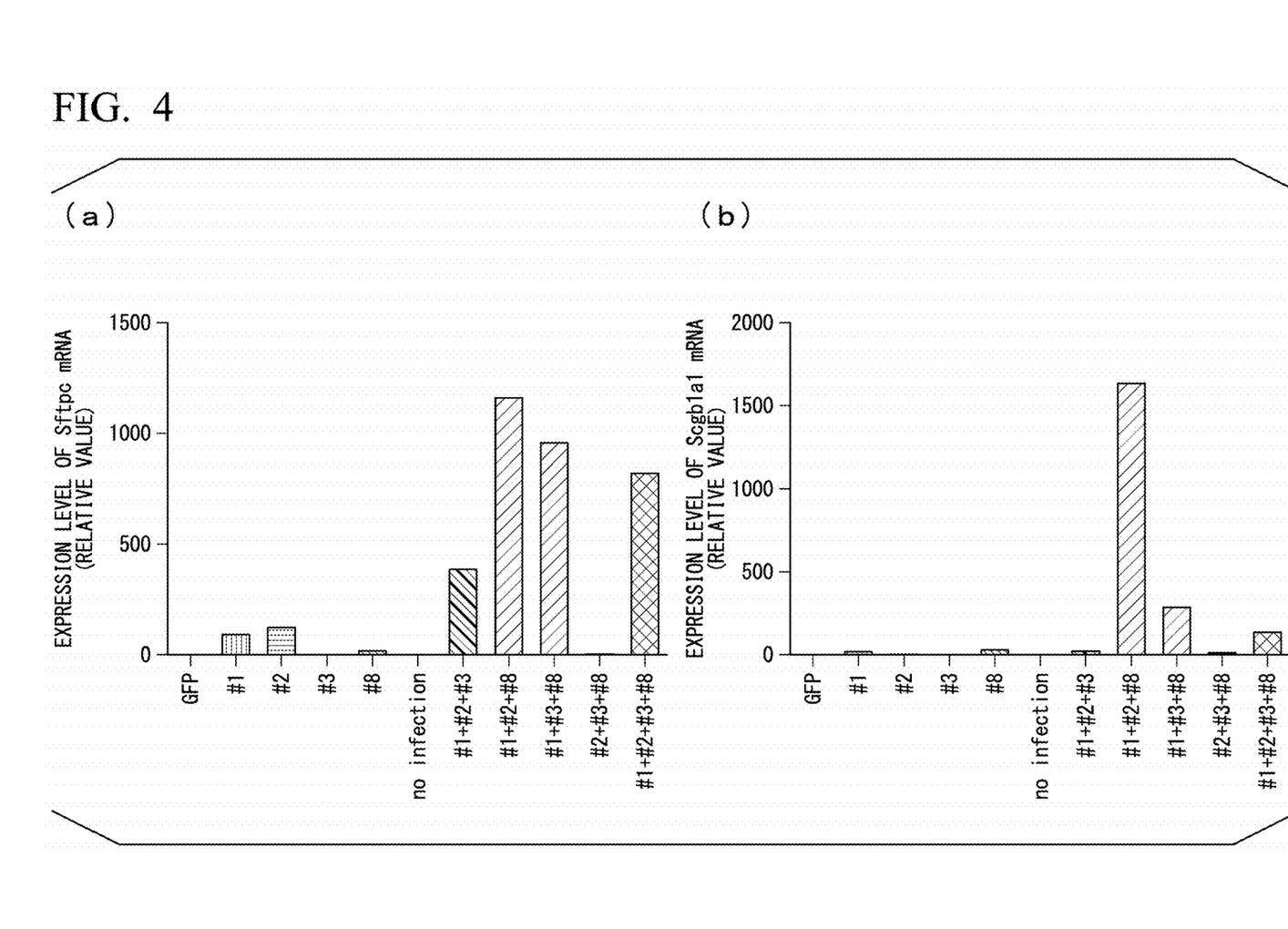

(a) of FIG. 4 is a graph showing results of measuring an mRNA expression level of an Sftpc gene. In addition, (b) of FIG. 4 is a graph showing results of measuring an mRNA expression level of an Scgb1a1 gene. In (a) and (b) of FIG. 4, the letter "GFP" indicates a result of the control cell, the letter "#1" indicates a result of introducing the gene of No. 1 in Table 1, and the letter "#1+#2+#3" indicates a result of introducing the genes of Nos. 1, 2, and 3 in Table 1 in combination, and the same applies to the residual letters. Furthermore, the letter "NO transfect" indicates a result of fibroblasts into which no gene was introduced.

As a result, it became clear that, in the fibroblasts into which these genes were introduced in combination, expression levels of the Sftpc gene and the Scgb1a1 gene increased. This result indicates that expression of the combination of these genes is important for differentiation-induction from fibroblasts into alveolar epithelial cells.

Experimental Example 5

(Examination 1 of Conditions for Differentiation from Somatic Cells to Alveolar Epithelial Cells)

An SPC-GFP mouse is a transgenic mouse into which a construct in which a GFP gene is linked downstream of an SPC (Sftpc) gene promoter is introduced. In the SPC-GFP mouse, GFP fluorescence is observed in cells that express the Sftpc gene. Herein, conditions for differentiation into alveolar epithelial cells from fibroblasts derived from an SPC-GFP mouse fetus as somatic cells were examined.

First, various combinations of the factor of No. 1 (an Nkx2-1 gene), the factor of No. 2 (a Foxa1 gene), the factor of No. 3 (a Foxa2 gene), and the factor of No. 8 (a Gata6 gene) shown in Table 1 were introduced into fibroblasts of the SPC-GFP mouse, followed by two-dimensional culture for 2 days, and GFP fluorescence was observed.

As combinations of factors, a combination of the factors of No. 1, No. 2, No. 3, and No. 8, a combination of the factors No. 1, No. 2, and No. 8, and a combination of the factors No. 1, No. 3, and No. 8 were examined.

As a result, the GFP fluorescence was not clearly detected. Meanwhile, as a result of measuring an expression level of the Sftpc gene by quantitative RT-PCR, it was checked that the mRNA expression level of the Sftpc gene increased.

Experimental Example 6

(Examination 2 of Conditions for Differentiation from Somatic Cells to Alveolar Epithelial Cells)

A total of four types of genes of the factor of No. 1 (an Nkx2-1 gene), the factor of No. 2 (a Foxa1 gene), the factor of No. 3 (a Foxa3 gene), and the factor of No. 8 (a Gata6 gene) shown in Table 1 were introduced into fibroblasts of the SPC-GFP mouse, and followed by two-dimensional culture for 1 to 2 days.

Thereafter, three-dimensional culture using Matrigel was performed. Various chemical factors were added to a medium for the three-dimensional culture. Table 2 shows chemical factors used and final concentrations thereof.

TABLE 2

| Chemical factor | Final concentration |
| --- | --- |
| Lactic acid | 1 mM |
| 8-Br-cAMP (CAS No.: 76939-46-3) | 0.1 mM |

TABLE 2-continued

| Chemical factor | Final concentration |
| --- | --- |
| IBMX (CAS No.: 28822-58-4) | 0.1 mM |
| Fibroblast Growth Factor 7 (FGF7) | 100 ng/mL |
| (NCBI Reference Sequence: NP_032034) | |
| Dexamethasone | 50 nM |
| Fibroblast Growth Factor 2 (FGF2) | 10 ng/mL |
| (NCBI Reference Sequence: NP_032032.1) | |
| Fibroblast Growth Factor 10 (FGF10) | 100 ng/mL |
| (NCBI Reference Sequence: NP_032028.1) | |
| CHIR-99021 (CAS No.: 252917-06-9) | 3 μM |

As a result, GFP-fluorescence-positive cells were observed 14 days after the gene introduction. In addition, 5% to 7% of the cells became GFP-fluorescence-positive 28 days after the gene introduction.

Figure 5:
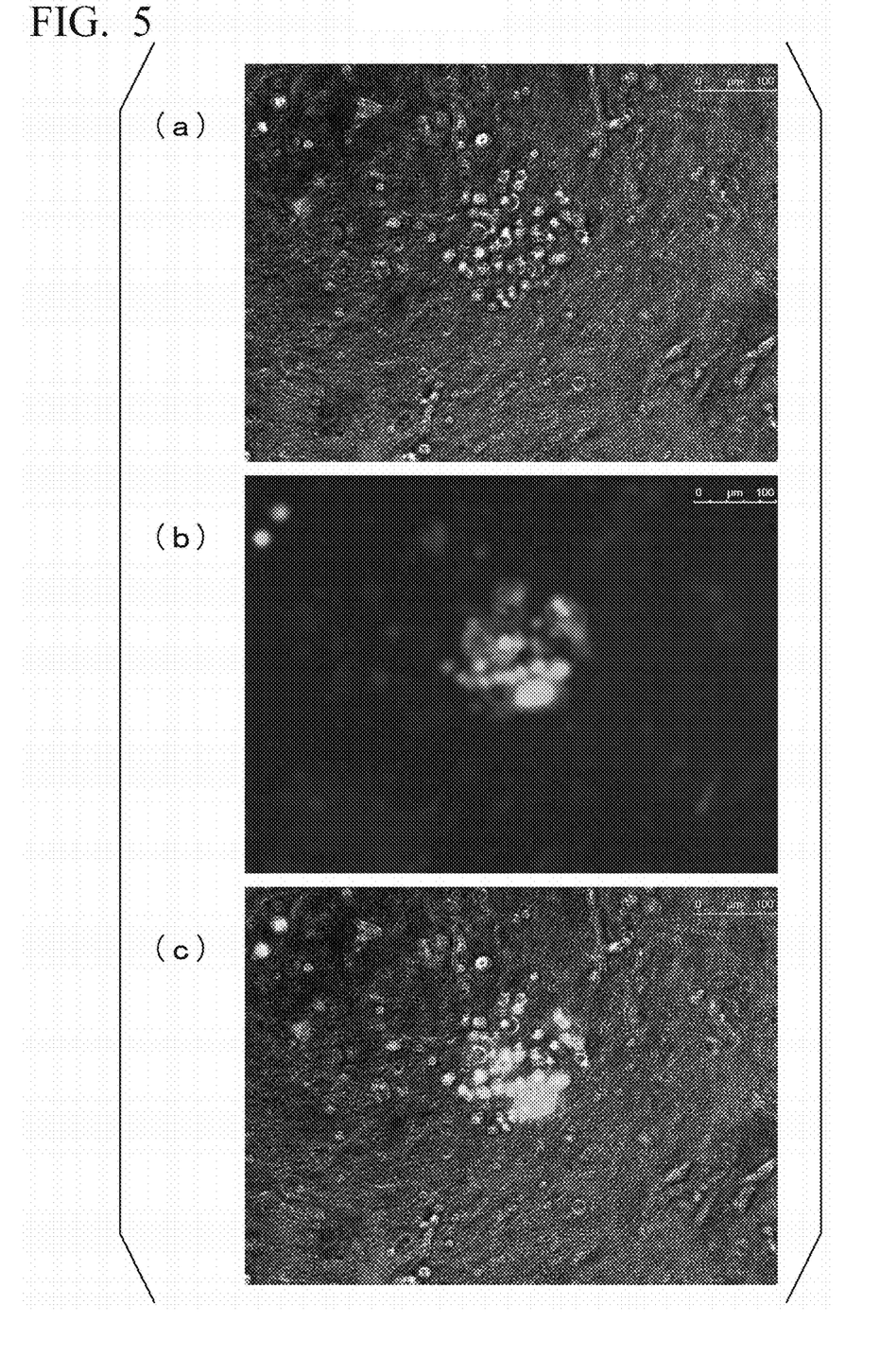

(a) to (c) of FIG. 5 are photomicrographs of cells 26 days after gene introduction. (a) of FIG. 5 is a bright-field observation image, (b) of FIG. 5 is a fluorescence micrograph of GFP fluorescence observed, and (c) of FIG. 5 is an image obtained by merging the images of (a) of FIG. 5 and (b) of FIG. 5.

Figure 6:
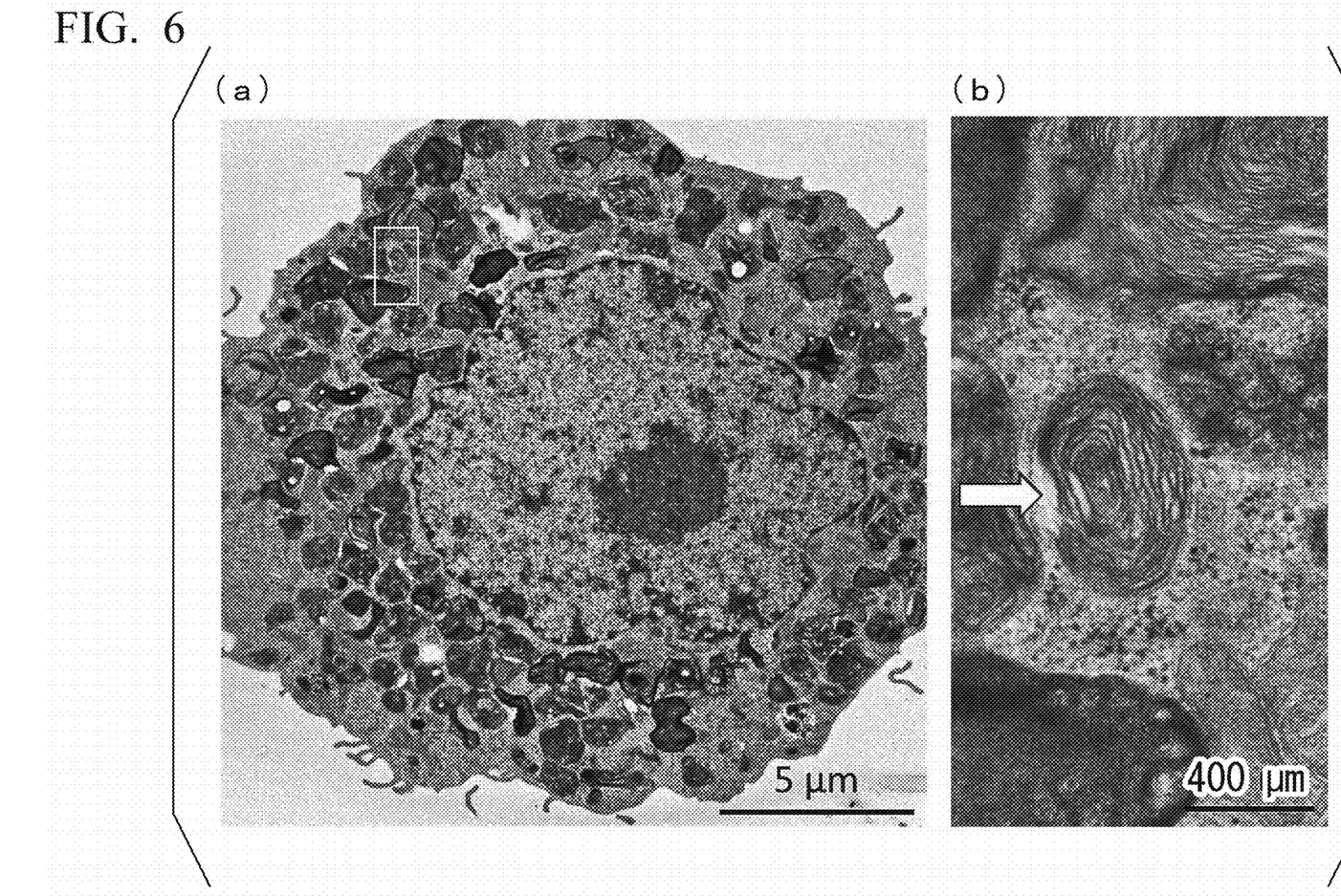

Subsequently, the obtained GFP-fluorescence-positive cells were recovered with a cell sorter and observed with an electron microscope. (a) and (b) of FIG. 6 are representative electron micrographs. (b) of FIG. 6 is an enlarged photograph of an area enclosed by a square in (a) of FIG. 6. As a result, it became clear that a structure called a lamellar body is present in the GFP-fluorescence-positive cells. In (b) of FIG. 6, an arrow indicates a lamellar body. The lamellar body is known to be a characteristic structure of type II alveolar epithelial cells. Based on these results, it became clear that cells derived from somatic cells were morphologically alveolar epithelial cells.

As a result of repeating the same experiment, the presence of the dexamethasone and the FGF family proteins (FGF2, FGF7, and FGF10) among chemical factors was considered to be particularly important to obtain the GFP-fluorescence-positive cells from somatic cells. In addition, among the FGF family proteins, the presence of FGF7 was considered to be particularly important.

Based on the above results, it became clear that performing three-dimensional culture of somatic cells that have undergone gene introduction, performing culture in the presence of the dexamethasone and the FGF family proteins, and the like can significantly increase efficiency of differentiation-induction from somatic cells into alveolar epithelial cells.

Experimental Example 7

(Examination 3 of Conditions for Differentiation from Somatic Cells to Alveolar Epithelial Cells)

A total of three types of genes of the factor of No. 1 (an Nkx2-1 gene), the factor of No. 2 (a Foxa1 gene), and the factor of No. 8 (a Gata6 gene) shown in Table 1; or a total of four types of genes of the factor of No. 1 (an Nkx2-1 gene), the factor of No. 3 (a Foxa2 gene), and the factor of No. 8 (a Gata6 gene) shown in Table 1 were respectively introduced into fibroblasts of the SPC-GFP mouse, and followed by three-dimensional culture in the same manner as in Experimental Example 6.

Figure 7:
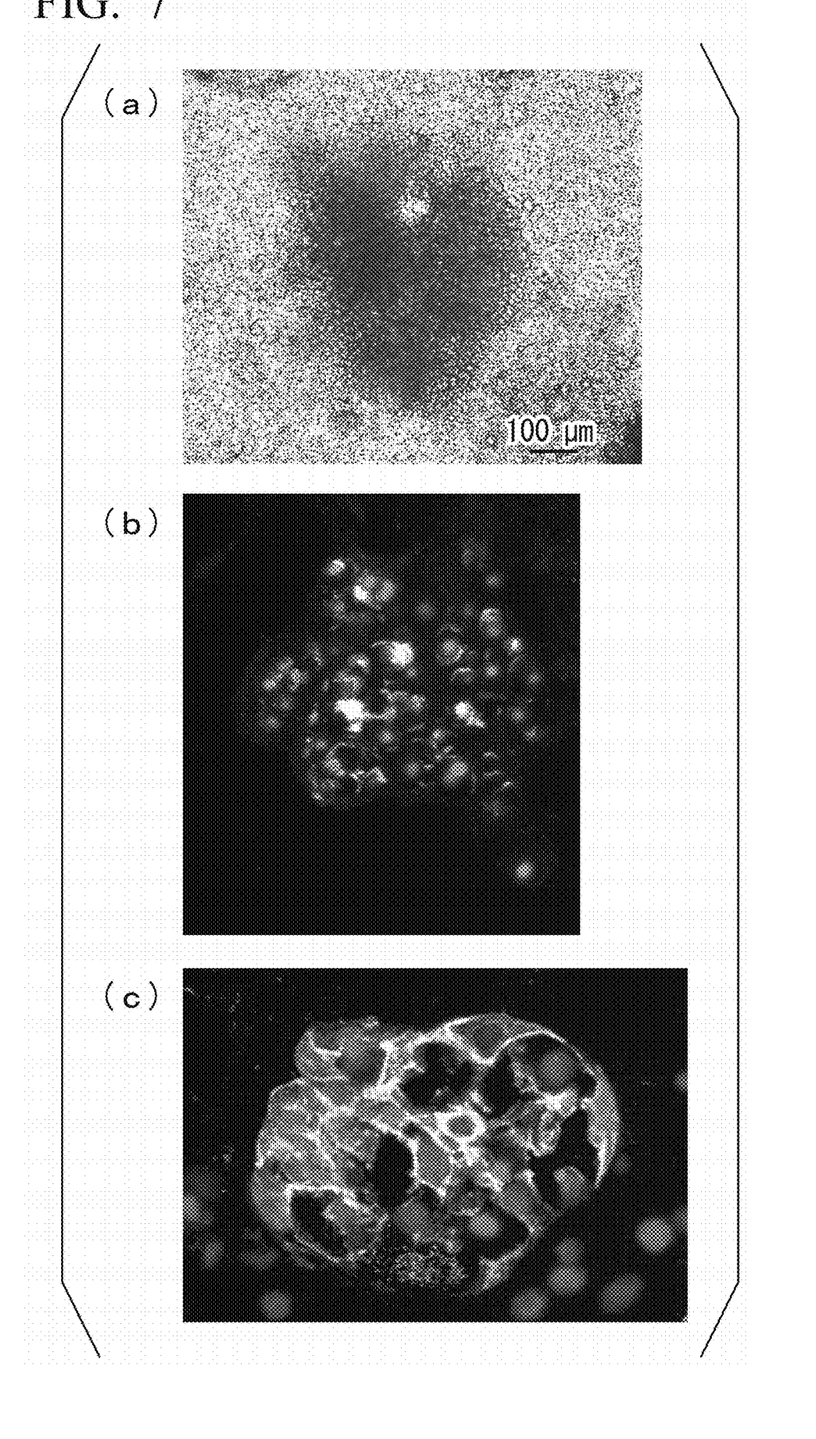

(a) of FIG. 7 is an image obtained by introducing a combination of a total of three types of genes of the factor of No. 1 (an Nkx2-1 gene), the factor of No. 2 (a Foxa1 gene), and the factor of No. 8 (a Gata6 gene) shown in Table 1 into a fibroblast; performing microscopic observation 12 days after the gene introduction; and merging a bright-field observation image and a fluorescence micrograph of GFP fluorescence observed.

As a result, it was checked that GFP-fluorescence-positive cells formed clusters 12 days after the gene introduction. The formation of clusters indicates that alveolar epithelial cells having a proliferative ability were obtained.

In addition, it was checked that the GFP-fluorescence-positive cells formed clusters 12 days after the gene introduction also in the fibroblasts into which the combination of a total of the three types of genes of the factor of No. 1 (an Nkx2-1 gene), the factor of No. 3 (a Foxa2 gene), and the factor of No. 8 (a Gata6 gene) shown in Table 1 were introduced.

Based on the above results, it became clear that alveolar epithelial cells can also be obtained by introducing the combination of the three types of genes.

Subsequently, fluorescent immunostaining was performed on the GFP-fluorescence-positive cells obtained by introducing, into fibroblasts, the combination of a total of the three types of genes of the factor of No. 1 (an Nkx2-1 gene), the factor of No. 2 (a Foxa1 gene), and the factor of No. 8 (a Gata6 gene) shown in Table 1. Then, expression of an SP-C (Sftpc) protein and an Aquaporin 5 (AQP5, an NCBI Reference Sequence of NP_033831.1) protein was examined. In addition, cell nuclei were stained with 4',6-diamidino-2-phenylindole (DAPI).

(b) of FIG. 7 is a fluorescence micrograph showing a result of staining an SP-C protein by fluorescent immunostaining. As a result, it was checked that the GFP-fluorescence-positive cells expressed the SP-C protein. Because the SP-C is mainly expressed in type II alveolar epithelial cells, it is generally regarded as a marker for the type II alveolar epithelial cells.

In addition, (c) of FIG. 7 is a fluorescence micrograph showing a result of staining an AQP5 protein by fluorescent immunostaining. As a result, it was checked that the GFP-fluorescence-positive cells expressed the AQP5 protein. Because the AQP5 is mainly expressed in type I alveolar epithelial cells, it is generally regarded as a marker for the type I alveolar epithelial cells.

The above results show that cells derived from somatic cells include both type I alveolar epithelial cells and type II alveolar epithelial cells.

Experimental Example 8

(Transplantation of Differentiation-Induced Alveolar Epithelial Cells into Influenza Mouse)

A mouse was nasally infected with a mouse-adapted influenza virus (A/H1N1, PR8) at a dose of 200 p.f.u./mouse. In addition, as a control, a mouse to which phosphate buffered saline (PBS) was administered instead of an influenza virus was prepared.

Subsequently, 1 hour later, $1 \times 10^6$ alveolar epithelial cells differentiation-induced from embryonic fibroblasts were transbronchially administered to the mice. In addition, for comparison, a mouse to which $1 \times 10^6$ embryonic fibroblasts that had not undergone differentiation-induction were transbronchially administered, and a mouse to which PBS was administered were also prepared.

<<Examination of Body Weight and Survival Rate>>

Figure 8:
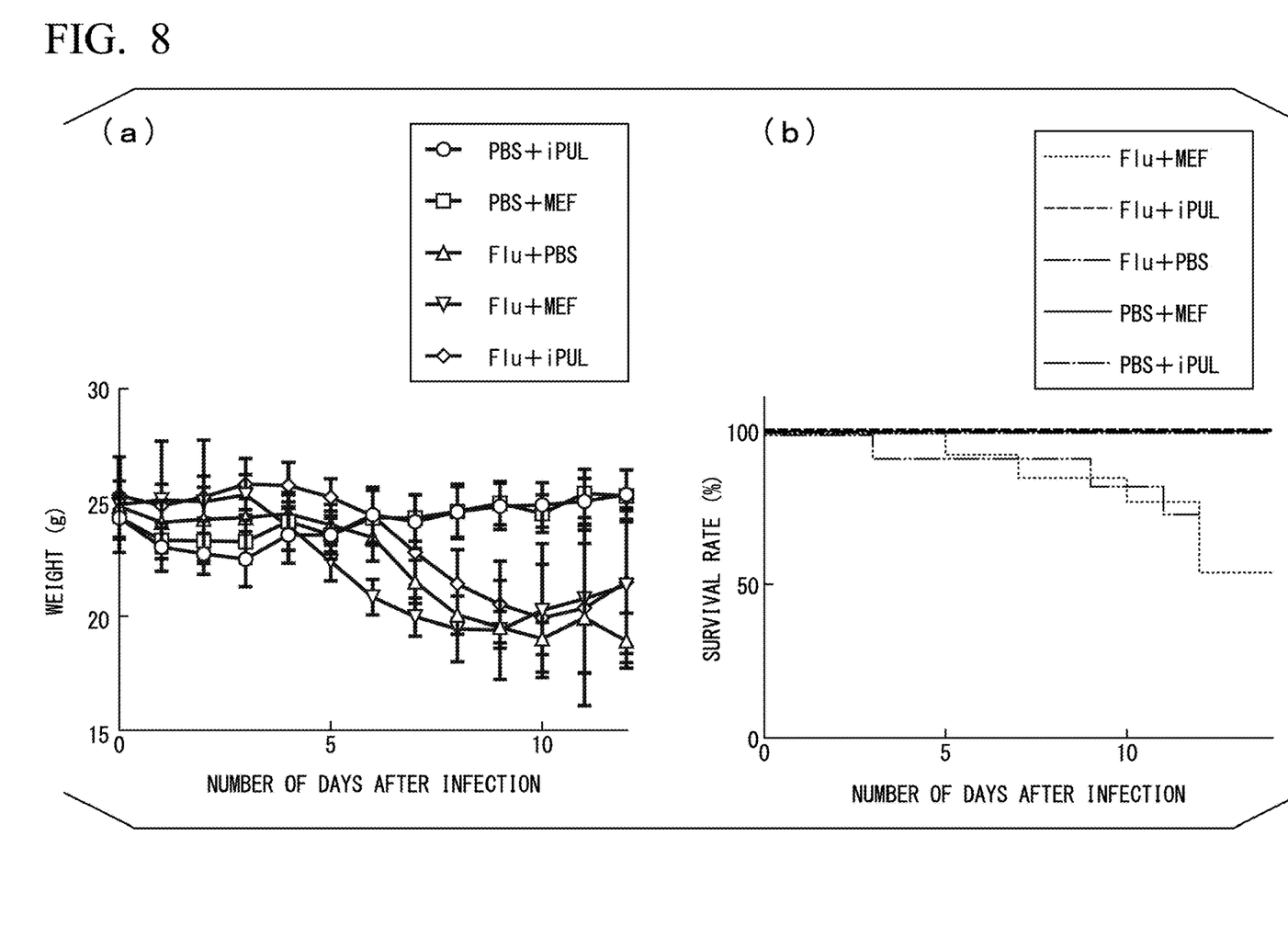

Subsequently, changes in body weight and survival rate of the mice in the respective groups were observed. (a) of FIG. 8 is a graph showing transitional changes in body weight of the mice in the respective groups, and (b) of FIG. 8 is a graph showing transitional changes in survival rate of the mice in the respective groups. In (a) and (b) of FIG. 8, the letter "Flu+iPUL" indicates results of a group in which mice were infected with an influenza virus, and then alveolar epithelial cells (iPUL) differentiation-induced from embryonic fibroblasts were administered to the mice; the letter "Flu+MEF" indicates results of a group in which mice were infected with an influenza virus, and then embryonic fibroblasts that had not undergone differentiation-induction were administered to the mice; the letter "Flu+PBS" indicates results of a group in which mice were infected with an influenza virus, and then PBS was administered to the mice; the letter "PBS+iPUL" indicates results of a group in which PBS was administered to mice, and then alveolar epithelial cells differentiation-induced from embryonic fibroblasts were administered to the mice; and the letter "PBS+MEF" indicates results of a group in which PBS was administered to mice, and then embryonic fibroblasts that had not undergone differentiation-induction were administered to the mice.

As a result, it was recognized that there was no significant difference in body weight loss due to influenza virus infection among the group in which alveolar epithelial cells differentiation-induced from embryonic fibroblasts were administered to the mice infected with an influenza virus; the group in which embryonic fibroblasts that had not undergone differentiation-induction were administered to the mice; and the group in which PBS was administered to the mice. On the other hand, it became clear that, in a case where alveolar epithelial cells differentiation-induced from embryonic fibroblasts were administered to the mice infected with an influenza virus, death due to influenza virus infection was significantly inhibited. A significant difference was observed in a survival rate of the "Flu+iPUL" group with respect to a survival rate of the "Flu+MEF" group at P=0.008.

<<Histochemical Analysis of Lung Tissue Sections>>

On the fifth day after infection with an influenza virus, lungs were excised from respective mice of the group (the Flu+iPUL group) in which the mice were infected with an influenza virus, and then alveolar epithelial cells differentiation-induced from embryonic fibroblasts were administered to the mice; and the group (the Flu+MEF group) in which the mice were infected with an influenza virus, and then embryonic fibroblasts that had not undergone differentiation-induction were administered to the mice. Subsequently, the excised lungs were fixed with 4% paraformaldehyde, and paraffin-embedded tissue sections were prepared. Subsequently, the tissue sections of the respective groups were deparaffinized with ethanol and pure water, stained with hematoxylin and eosin, and observed with an optical microscope.

Figure 9:
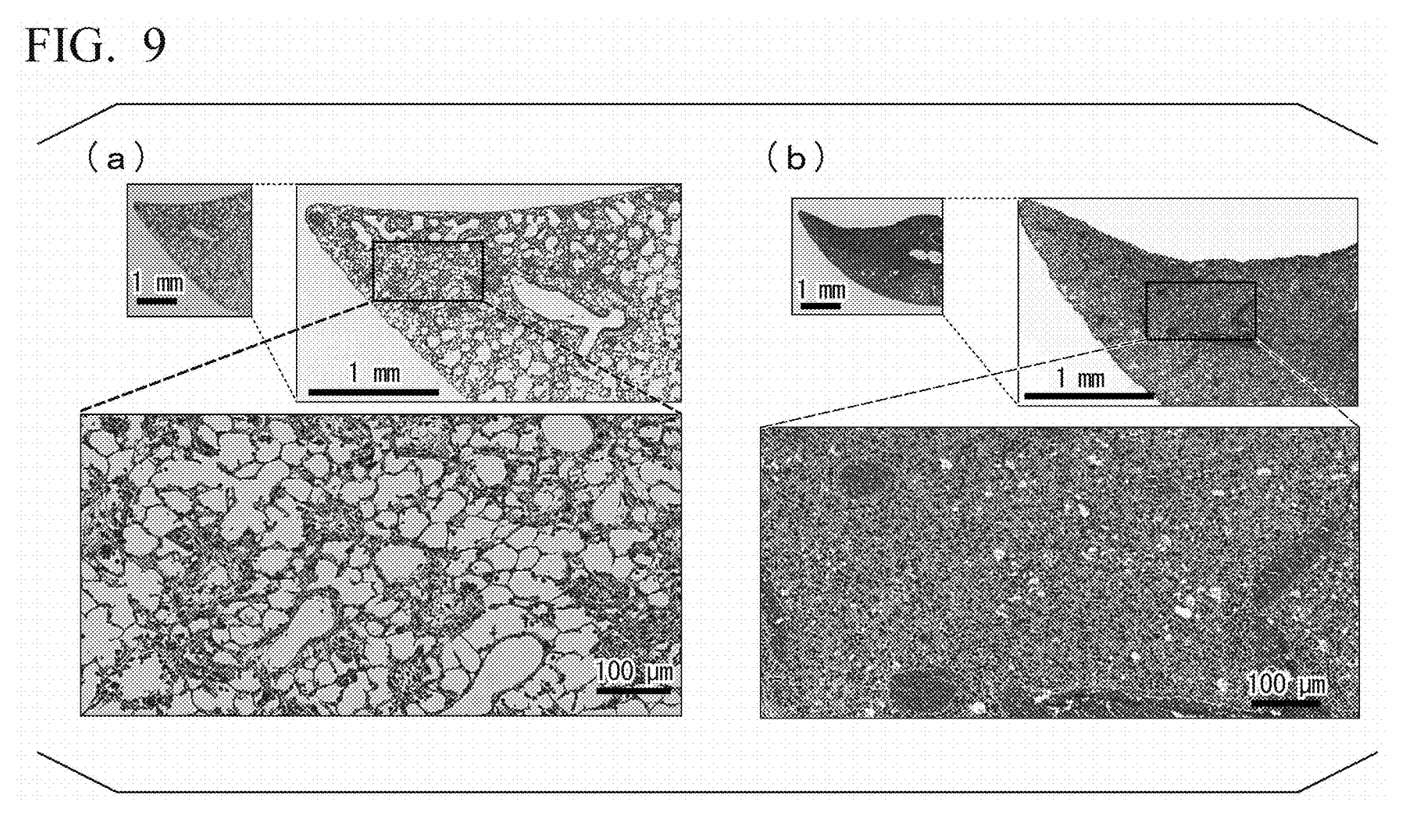

(a) of FIG. 9 is a photomicrograph of a tissue section of the lung of the Flu+iPUL group. In addition, (b) of FIG. 9 is a photomicrograph of a tissue section of the lung of the Flu+MEF group. As a result, in the Flu+iPUL group, it became clear that lung damage due to influenza virus infection was inhibited. On the other hand, in the Flu+MEF group, it became clear that lung damage due to influenza virus infection could not be inhibited.

<<Fluorescent Immunostaining of Lung Tissue Sections>>

Subsequently, the lung tissue sections of the Flu+iPUL group were immunostained to examine expression of the GFP protein and the SP-C protein.

Figure 10:
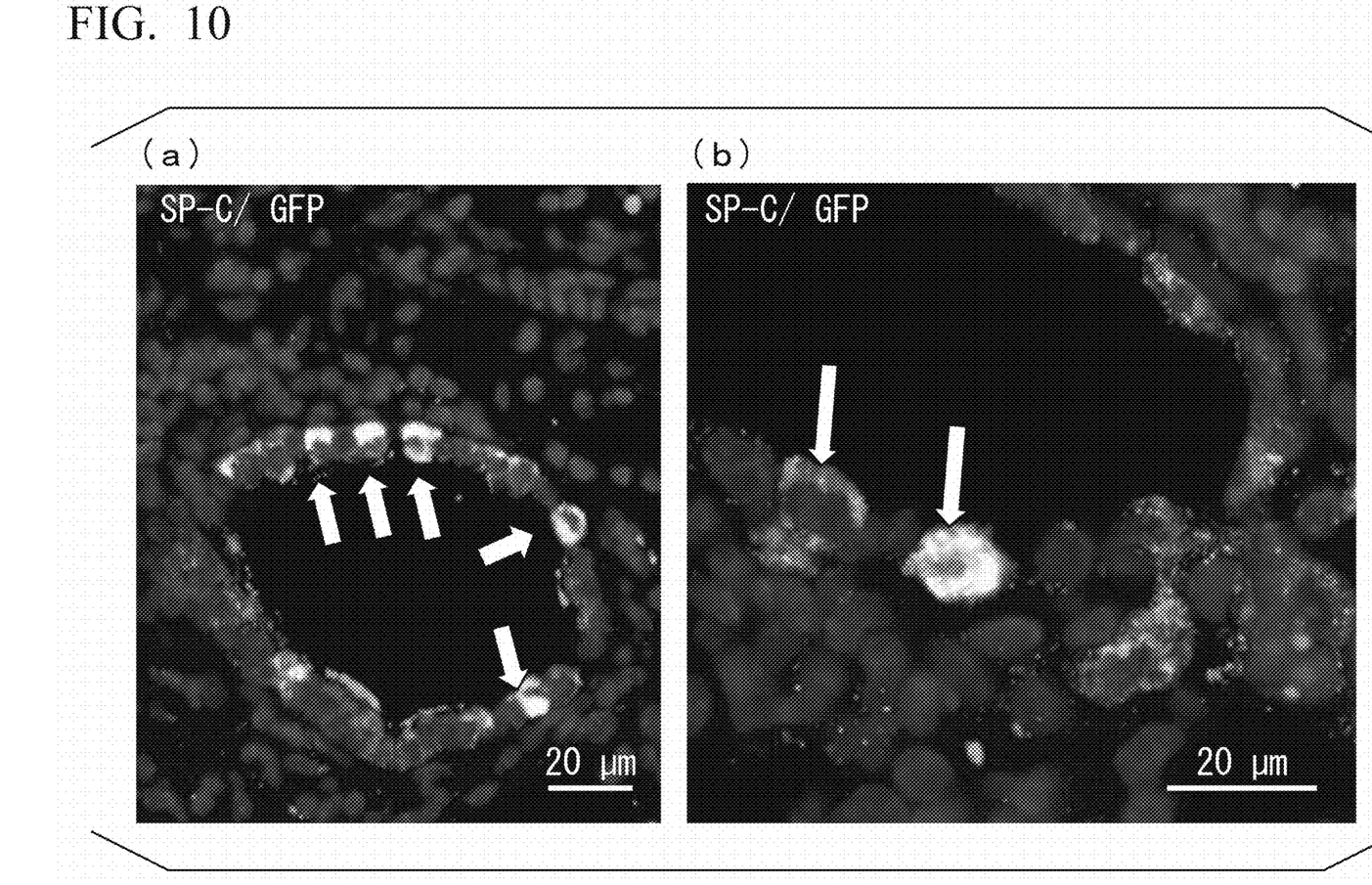

(a) and (b) of FIG. 10 are representative fluorescence micrographs showing results of immunostaining. (a) and (b) each have different fields of view and magnifications. In (a) and (b) of FIG. 10, GFP protein(+)/SP-C protein(+) double-positive cells are indicated by arrows.

As a result, the presence of the GFP protein(+)/SP-C protein(+) double-positive cells was checked. Based on this result, it was checked that alveolar epithelial cells differentiation-induced from embryonic fibroblasts were engrafted in the lung of the Flu+iPUL group.

Experimental Example 9

(Differentiation-Induction from Human Fibroblasts to Alveolar Epithelial Cells)

A combination of a human NKX2-1 gene, a human FOXA1 gene, a human FOXA2 gene, and a human GATA6 gene was introduced into human dermal fibroblasts (cell name "HDFa," Thermo Fisher Scientific), and whether these human dermal fibroblasts can be differentiation-induced into alveolar epithelial cells or not was examined as in the case of the mice.

As gene combinations, a combination of three genes of a human NKX2-1 gene, a human FOXA1 gene, and a human GATA6 gene; a combination of three genes of a human NKX2-1 gene, a human FOXA2 gene, and a human GATA6 gene; and a combination of four genes of a human NKX2-1 gene, a human FOXA1 gene, a human FOXA2 gene, and a human GATA6 gene were examined.

For introduction of respective genes, a retrovirus system (type "pMX," Cell Biolabs) was used. In addition, Plat-GP cells (Cell Biolabs) were used as packaging cells.

Three-dimensional culture of HDFa cells into which respective genes were introduced started on the second day from the gene introduction using a Matrigel. Subsequently, on the 11th day and the 17th day from the gene introduction, expression levels of the SFTPC gene in the respective cells were measured by quantitative RT-PCR.

Figure 11:
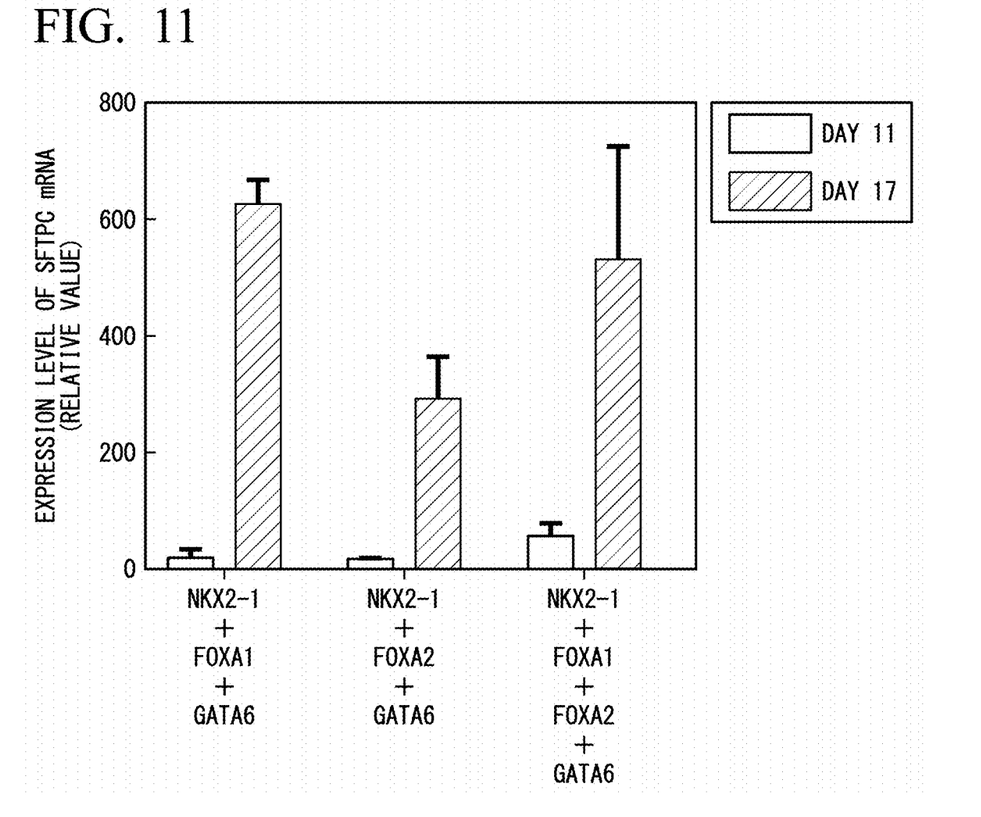
FIG. 11 is a graph showing results of measuring an mRNA expression level of an SFTPC gene in a human dermal fibroblast line (an HDFa cell) into which a human NKX2-1 gene, a human FOXA1 gene, a human FOXA2 gene, and a human GATA6 gene were introduced in various combinations in Experimental Example 9.

FIG. 11 is a graph showing results of quantitative RT-PCR. In FIG. 11, an expression level of the SFTPC gene is shown using a relative value in which an expression level of the SFTPC gene in the HDFa cells into which the gene had not been introduced is 1.

As a result, in the HDFa cells into which the combination of the three genes of the human NKX2-1 gene, the human FOXA1 gene, and the human GATA6 gene was introduced, it became clear that, on the 17th day from the gene introduction, an expression level of the SFTPC gene reached about 630 times that of the HDFa cells into which the gene had not been introduced.

In addition, in the HDFa cells into which the combination of the three genes of the human NKX2-1 gene, the human FOXA2 gene, and the human GATA6 gene was introduced, it became clear that, on the 17th day from the gene introduction, an expression level of the SFTPC gene reached about 290 times that of the HDFa cells into which the gene had not been introduced.

Furthermore, in the HDFa cells into which the combination of the four genes of the human NKX2-1 gene, the human FOXA1 gene, the human FOXA2 gene, and the human GATA6 gene was introduced, it became clear that, on the 17th day from the gene introduction, an expression level of the SFTPC gene reached about 520 times that of the HDFa cells into which the gene had not been introduced.

Based on the above results, it became clear that, in the case of humans as well as the case of the mice, somatic cells can be differentiation-induced into alveolar epithelial cells by allowing the somatic cells to express the combination of the NK2 homeobox family gene, the Fox family gene, and the Gata family gene.

INDUSTRIAL APPLICABILITY

According to the present invention, it is possible to provide a technique for manufacturing alveolar epithelial cells more simply without using stem cells.

The invention claimed is:

1. A kit for differentiating somatic cells into alveolar epithelial cells, the kit comprising:
   an expression vector including an NK2 homeobox family gene;
   an expression vector including a Forkhead box (Fox) family gene, and
   an expression vector including a Gata family gene,
   wherein the Gata family gene is a Gata Binding Protein 6 (Gata6) gene.

2. The kit for differentiating somatic cells into alveolar epithelial cells according to claim 1, wherein the Fox family gene is a Forkhead Box A1 (Foxa1) gene or a Forkhead Box A2 (Foxa2) gene.

3. A kit for differentiating somatic cells into alveolar epithelial cells, the kit comprising:
   an expression vector including an NK2 homeobox family gene; and
   an expression vector including a Forkhead box (Fox) family gene;
   wherein the NK2 homeobox family gene is an NK2 Homeobox 1 (Nkx2-1) gene.

4. The kit for differentiating somatic cells into alveolar epithelial cells according to claim 3, wherein the Fox family gene is a Forkhead Box A1 (Foxa1) gene or a Forkhead Box A2 (Foxa2) gene.

5. A method for manufacturing mouse or human alveolar epithelial cells expressing a Surfactant Protein C (Sftpc) gene and a Secretoglobin Family 1A Member 1 (Scgb1a1) gene, the method comprising:
   introducing an expression vector including an NK2 homeobox family gene and an expression vector including a Forkhead box (Fox) family gene into a mouse or human fibroblast cell derived from a mouse fetus or human dermal fibroblast, respectively to express the NK2 homeobox family gene and the Forkhead box (Fox) family gene;
   culturing the mouse or human fibroblast cell after introducing the expression vectors; and
   inducing differentiation of the mouse or human fibroblast cell into the mouse or human alveolar epithelial cell, respectively.

6. The manufacturing method according to claim 5, wherein an expression vector including a Gata family gene is further introduced into the mouse or human fibroblast cell derived from a mouse fetus or human dermal fibroblast, respectively to express the NK2 homeobox family gene, the Fox family gene and the Gata family gene.

7. The manufacturing method according to claim 5, wherein the culturing is performed by three-dimensional culture.

8. The manufacturing method according to claim 5, wherein the culturing step is performed in the presence of dexamethasone and a Fibroblast Growth Factor (FGF) family protein.

* * * * *